US007101347B2

(12) United States Patent
Culhane et al.

(10) Patent No.: US 7,101,347 B2

(45) Date of Patent: Sep. 5, 2006

(54) COMBINATION PRO/SUPINATION AND FLEXION THERAPEUTIC MOBILIZATION DEVICE

(75) Inventors: Jeff Culhane, Phoenix, AZ (US); Alex Solomon, Mississauga (CA); Paul Kruger, Toronto (CA); Dragan Milosavljevic, Toronto (CA); Dan Cotterell, Ajax (CA); Andrew MacPhail, Toronto (CA)

(73) Assignee: OrthoRehab., Inc., Lowell, MA (US)

( * ) Notice: Subject to any disclaimer, the term of this patent is extended or adjusted under 35 U.S.C. 154(b) by 0 days.

(21) Appl. No.: 10/436,465

(22) Filed: May 13, 2003

(65) Prior Publication Data

US 2004/0082885 A1 Apr. 29, 2004

Related U.S. Application Data

(63) Continuation of application No. 09/689,812, filed on Oct. 13, 2000, now abandoned.

(60) Provisional application No. 60/189,051, filed on Mar. 14, 2000.

(51) Int. Cl.
*A61F 5/00* (2006.01)

(52) U.S. Cl. ............................ 602/5; 602/21; 128/877; 128/879

(58) Field of Classification Search .................... 602/5, 602/21, 20; 128/877, 878, 879, 881
See application file for complete search history.

(56) References Cited

U.S. PATENT DOCUMENTS 4,538,595 A 9/1985 Hajianpour
5,102,411 A 4/1992 Hotchkiss et al.
5,117,814 A 6/1992 Luttrell et al.
5,219,323 A * 6/1993 Singer et al. ................. 601/33
5,637,076 A * 6/1997 Hazard et al. ........... 297/284.6
5,683,353 A * 11/1997 Hamersly .................... 601/33
5,848,979 A * 12/1998 Bonutti et al. ................ 482/45
5,951,499 A * 9/1999 Saringer et al. .............. 601/33

* cited by examiner

*Primary Examiner*—Henry Bennett
(74) *Attorney, Agent, or Firm*—Nancy E. Hill; Hill & Schumacher

(57) ABSTRACT

A therapeutic mobilization device is disclosed. The device includes a flexion assembly, a pro/supination assembly and a valgus carrying angle compensation device. The flexion assembly has an arm attachment assembly and an elbow actuator and the elbow actuator defines and axes of rotation. The pro/supination assembly is attached to flexion assembly and has a distal forearm attachment assembly and a pro/supination actuator operably connected thereto. The valgus carrying angle compensation device is operably attached to the flexion assembly and the pro/supination assembly. Preferably the pro/supination assembly is slidably mounted on a housing shaft whereby during flexion the pro/supination assembly is free to move along the housing shaft. Further, preferably the arm attachment assembly includes an attachment ring and an adjustable clamp pivotally attached thereto whereby the attachment ring defines a pro/supination axis and the adjustable clamp pivots orthogonally to the pro/supination axis.

21 Claims, 14 Drawing Sheets

COMBINATION PRO/SUPINATION AND FLEXION THERAPEUTIC MOBILIZATION DEVICE

CROSS REFERENCE TO RELATED PATENT APPLICATION

This patent application is a continuation application of U.S. patent application, Ser. No. 09/689,812 filed on Oct. 13, 2000 now abandoned entitled COMBINATION PRO/SUPINATION AND FLEXION THERAPEUTIC DEVICES with the same inventors, which is related to U.S. Provisional Patent Application, Ser. No. 60/189,051 filed on Mar. 14, 2000 entitled A COMBINATION PRO/SUPINATION AND FLEXION THERAPEUTIC MOBILIZATION DEVICE.

FIELD OF THE INVENTION

This invention relates to therapeutic mobilization and splinting devices and in particular a combination pro/supination and flexion device.

BACKGROUND OF THE INVENTION

In recent years it has become evident that the rehabilitation and treatment of injured joints and surrounding soft tissue can be expedited by use of continuous passive motion (CPM) static and dynamic serial splinting of the involved joint and surrounding soft tissue. CPM and splinting entails moving the joint via its related limbs through a passive controlled range of motion without requiring any muscle coordination. Active motion is also beneficial to the injured joint, however muscle fatigue limits the length of time the patient can maintain motion or positioning, therefore a device that provides continues passive motion to the joint is essential to maximize rehabilitation results. Numerous studies have proven the clinical efficacy of CPM or splinting to accelerate healing and maintain a range of motion. Static Progressive Splinting (SPS) and Dynamic Splinting (DS) are accepted and effective treatment modalities for the management and modelling of soft tissue surrounding articulations. Both SPS and DS have been proven efficacious and are supported by clinical studies. CPM, SPS and DS are integral components of a successful therapy protocol.

The successful rehabilitation of elbow and forearm injuries is complex, time consuming and often challenging due to the mobility, complex geometry and high stresses in and around the joint.

SUMMARY OF THE INVENTION

The therapeutic mobilization device of the present invention includes a flexion assembly, a pro/supination assembly and a valgus carrying angle compensation device. The flexion assembly has an arm attachment assembly and an elbow actuator and the elbow actuator defines and axes of rotation. The pro/supination assembly is attached to flexion assembly and has a distal forearm attachment assembly and a pro/supination actuator operably connected thereto. The valgus carrying angle compensation device is operably attached to the flexion assembly and the pro/supination assembly.

In another aspect of the present invention the therapeutic mobilization device includes an arm attachment assembly, a distal forearm attachment assembly, and elbow actuator and a valgus carrying angle compensation device. The compensation device is connected between the arm attachment assembly and the distal forearm attachment assembly. The elbow actuator is operably connected to the arm attachment assembly and the distal forearm attachment assembly whereby movement of the actuator causes the user's elbow to move through flexion.

In a further aspect of the invention the therapeutic mobilization device includes an arm attachment assembly, a distal forearm attachment assembly and an elbow actuator. The distal forearm attachment assembly includes a housing shaft and an adjustable clamping mechanism slidably mounted on the housing shaft. The elbow actuator is operably connected to the arm attachment assembly and the housing ring whereby movement of the actuator causes the user's elbow to move through flexion and the adjustable clamping mechanism is free to move along the housing shaft.

In a still further aspect of the invention a therapeutic mobilization device includes a pro/supination actuator and a pro/supination assembly. The pro/supination assembly includes a pro/supination housing, an attachment ring rotatably attached to the housing and a distal forearm attachment assembly attached thereto. A belt is attached to the attachment ring and to the pro/supination actuator whereby actuation of the pro/supination actuator causes the belt to move the attachment ring in pronation and supination.

It is an object of the present invention to provide continuous passive motion and/or electronically controlled progressive splinting device. The device will have two operating modes. The first and default-operating mode may be CPM. CPM typically involves defining a range of motion (ROM) within which a device operates. A pause can be added at the end of the direction of travel prior to the device returning to the other programmed extreme of motion. This operational mode promotes the maintenance of a joint's ROM. CPM devices are typically configured with a Reverse On Load (ROL) safety feature. The ROL is the level of force or resistance required to reverse the direction of travel or rotation of a CPM device.

The device may be suitable for bed, chair and ambulatory use configurations. The device may be symmetrical and ambidextrous. The device provides a full range of variable elbow flexion. The device also provides a full range of variable pronation and supination motion for the forearm. These motions are available in a synchronized motion, independently or in a serial motion. If pro/supination serial motion is chosen, preferably pro/supination will occur at 90 degrees of elbow flexion or as close thereto as possible. This is to limit stress on the joints. Preferably the device is controlled by a hand-held user interface which allows the operator to adjust the speed of travel (CPM mode only), range of motion, pause time at end of cycle and reverse on load. Preferably the device includes a means to electronically lock the patient settings while still allowing the patient to adjust the speed.

The orthosis of the device is configured to provide anatomical elbow flexion and forearm pro/supination. The orthosis also compensates for the valgus carrying angle. The valgus carrying angle is the result of the lateral migration of the distal radius and ulna relative to the distal humerus as the forearm pro/supinates. The orthosis may also compensates for the anthropometric variances between patients. This is achieved by accommodating differences in arm circumference, length and anatomical axis relative to the exterior surfaces of the arm. The device integrates a novel arrangement of strain gauges to monitor the amount of force in flexion and torque in pro/supination the device is delivering to the involved limb.

The invention relates to continuous passive motion (CPM) and progressive splinting devices for the synovial joints and surrounding soft tissue of the human body. The device forming the present invention comprises proximal and distal humerus supports. The humerus supports are allowed to move telescopically relative to each other, where the distal humerus support is suitably fixed to the chassis of the device. The device also comprises a distal radius and ulna support. The radius and ulna supports move in rotation relative to the humerus supports to provide pro/supination. The distal radius and ulna support also moves in a planer motion relative to the humerus supports to provide elbow flexion. The device includes two microprocessor controlled electric actuators. The actuators are located at the elbow and distal forearm. The actuators are suitably fixed to the orthosis and provide rotational motion concentric with the elbow and forearm's anatomic axis. The elbow actuator is a simple pivot actuator whereby a mechanical pivot is concentric with the device's elbow anatomical axis.

In typical CPM mode the ROM is defined and the device operates through a consistent defined range. An alternate configuration of elbow anatomical axis compensation includes two semicircular shapes slidably mounted to each other. This configuration can achieve similar results in providing one adjustment to compensate for circumference and position of the elbow's anatomic axis relative to the upper arm.

Further features of the invention will be described or will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Figure 1:
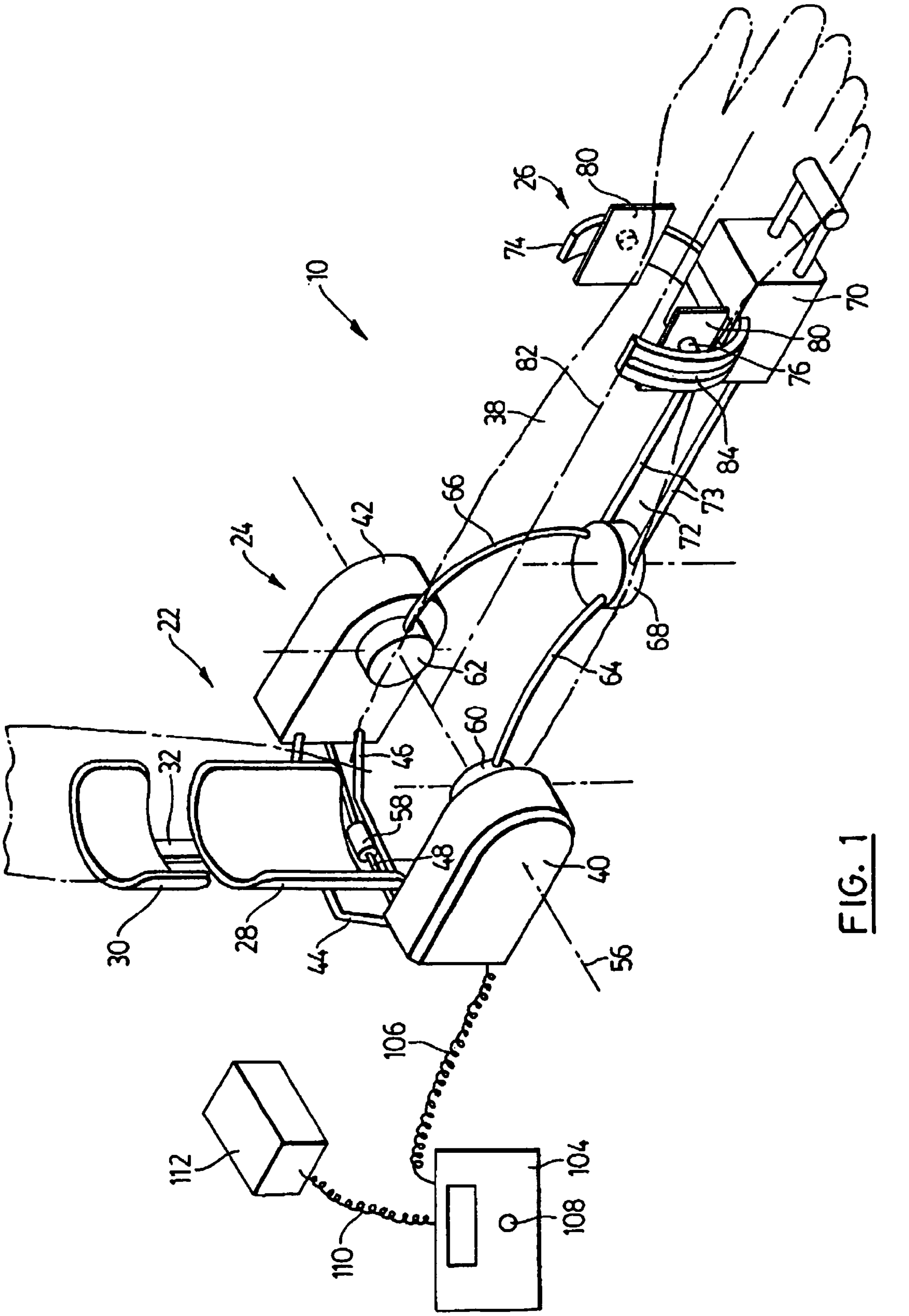
FIG. 1 is a perspective view the combination pro/supination and flexion therapeutic mobilization device constructed in accordance with the present invention.
Figure 3:
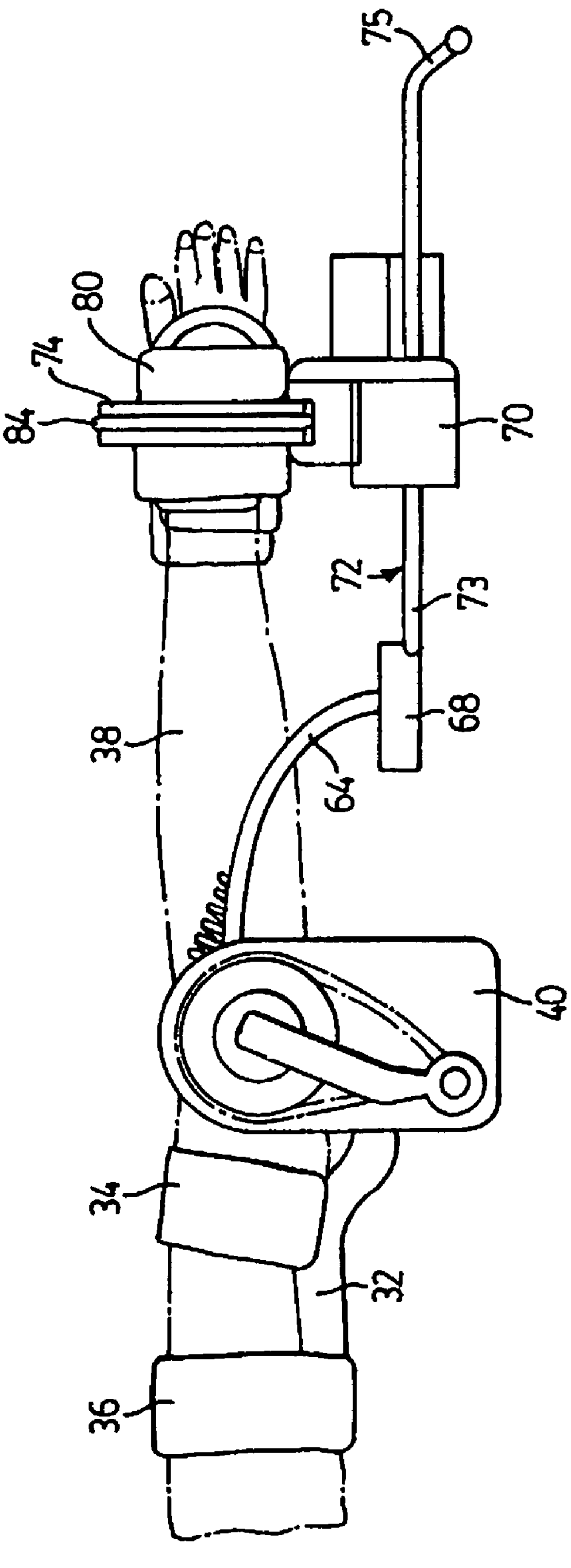
FIG. 3 is a side view of the combination pro-supination and flexion therapeutic mobilization device.
Figure 4:
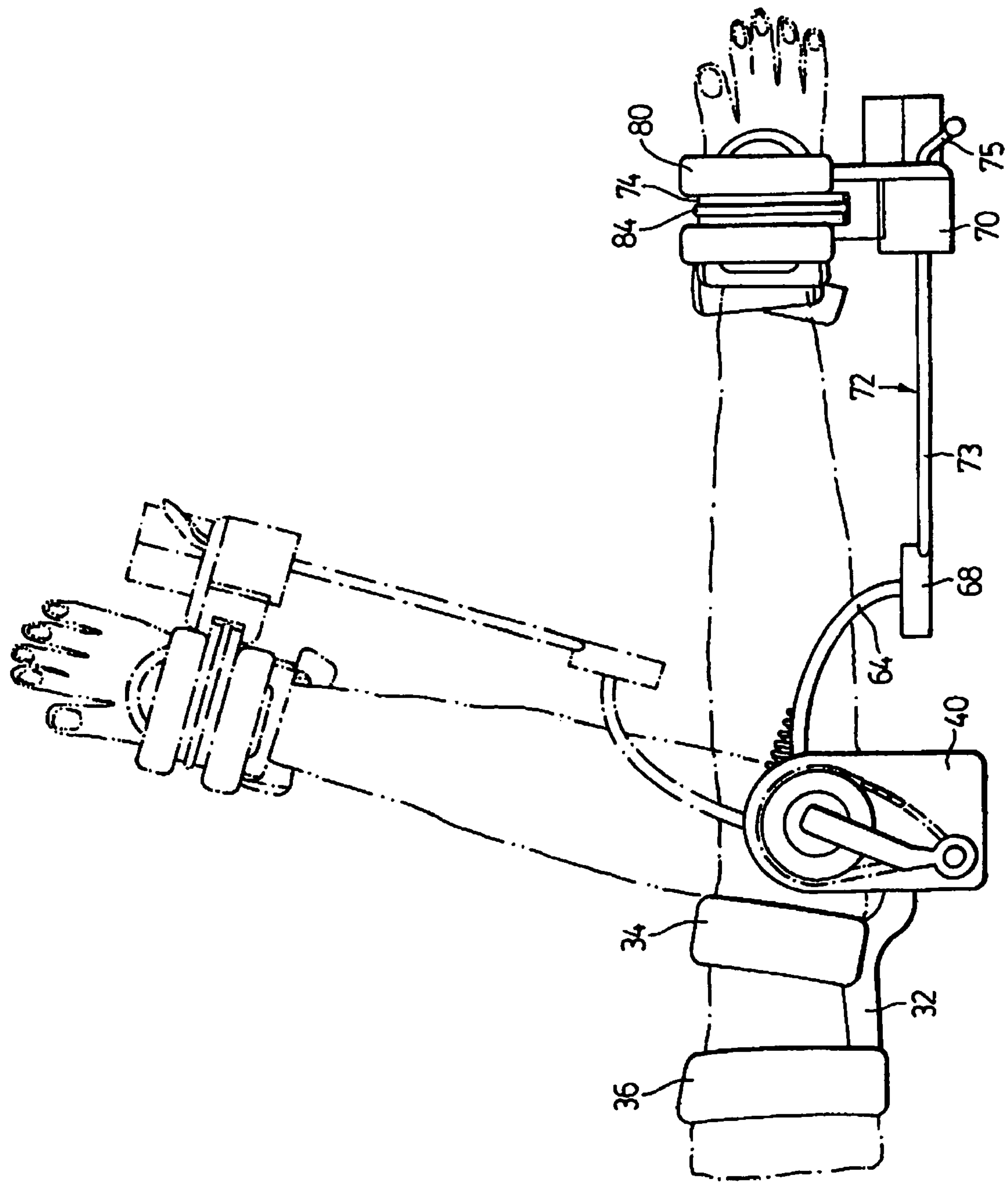
FIG. 4 is a side view of the combination pro-supination and flexion therapeutic mobilization device showing the device in two positions for the device.

Referring to FIGS. 1 and 3 an elbow and wrist therapeutic mobilization device or pro/supination flexion mobilization device is shown generally at 10. The device includes an upper arm or humerus support 22, an elbow or flexion assembly 24 and a wrist or pro/supination assembly 26.

The upper arm or humerus support 22 includes a lower or distal humerus cuff 28 and an upper or proximal humerus cuff 30. Cuff 30 is slidably mounted along cuff support 32. A lower cuff strap 34 (shown in FIG. 3) is attached to the lower humerus cuff 28 and an upper cuff humerus strap 36 is attached to the proximal humerus cuff 30. Straps 34 and 36 use hook and loop type fastener to allow for easy attachment and adjustment. The distance between the lower humerus cuff 28 and the proximal humerus cuff 30 can be adjusted to ensure that device 10 is securely attached to the patient, shown in phantom at 38.

Figure 2:
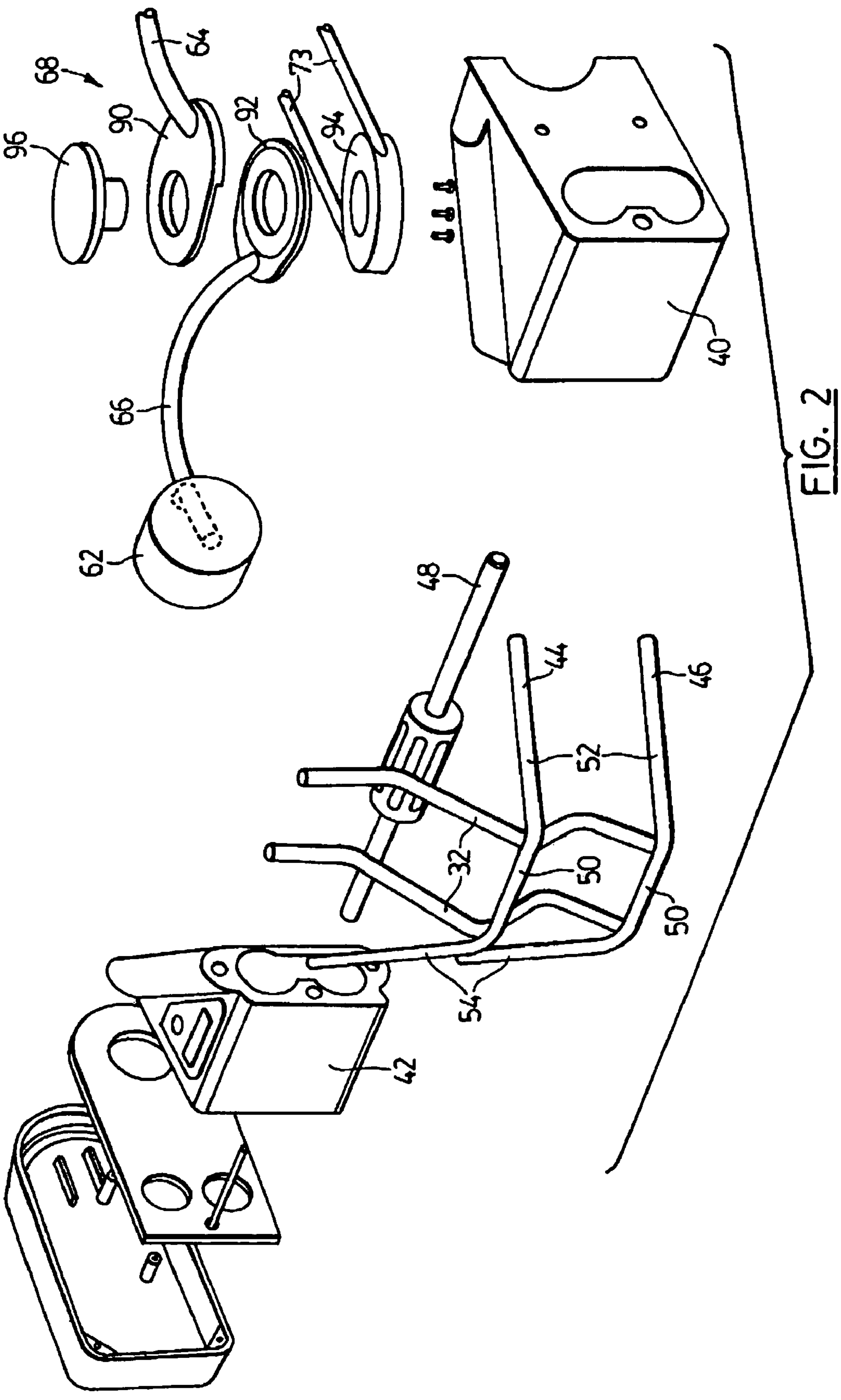
FIG. 2 is an exploded perspective view of the flexion assembly and the pivot of the combination pro/supination and flexion therapeutic mobilization device.

The elbow assembly 24, as shown in FIGS. 1 and 2, includes first and second elbow actuators 40 and 42 respectively, spaced apart top and bottom orthosis rods 44 and 46 respectively and barrel nut assembly 48. Top and bottom orthosis rods 44 and 46 each have a back portion 50 and forwardly and outwardly extending first and second side portions 52 and 54 respectively. The first 40 and second 42 elbow actuators are slidably mounted on the side portions 52, 54 of the top 44 and 46 bottom orthosis rods. One of the first 40 and second 42 elbow actuators is a drive flexion elbow actuator and the other may be an idler elbow actuator. Elbow actuators 40, 42 each have an elbow axis of rotation 56 that is co-linear. Barrel nut assembly 48 is attached with threaded type connections at one end to the first elbow actuator 40 and at the other end to the second elbow actuator 42. Rotation of the nut 58 in one direction causes the elbow actuators 40 and 42 to move toward each other and rotation in the other direction causes them to move away from each other. As the elbow actuators 40, 42 move relative to each other the elbow axis of rotation 56 remains co-linear.

The elbow assembly 24 is arranged such that it can easily be adjusted to accommodate patients with different sized elbows and different position of the elbow axis or rotation relative to the humerus support 22. As the first and second elbow actuators 40 and 42 slidably move along top 44 and bottom 46 orthosis rods away from each back portion 50 thereof the distance of the elbow axis 56 relative to humerus support 22 proportionately increases and the distance between the first 40 and second 42 elbow actuators increases. Accordingly by adjusting the barrel nut assembly 48 the patient or health care assistant uses one motion and adjustment to accommodate differences in upper arm circumferences and differences in position of the arm elbow anatomic axis relative to the posterior surface of the arm.

The first 40 and second 42 actuators have corresponding first 60 and second 62 rotating shafts respectively. Rotating shafts 60 and 62 rotate in a concentric fashion with the elbow axis 56. First 64 and second 66 drive stays are connected at one end to first 60 and second 62 rotating shafts respectively. At the other end first 64 and second 66 drive stays are connected to valgus pivot 68. Pro-supination assembly 26 is attached to valgus pivot 68.

Pro-supination assembly 26 includes a pro/supination housing 70, housing shaft 72, a ring assembly 74 and a ulna clamping device 76. Housing shaft 72 includes a pair of parallel rods 73. Pro/supination housing 70 is slidably mounted to parallel rods 73 so that it can easily move along the rods during use. Rods 73 include a bent portion 75 at the distal end thereof which limits movement of the pro/supination housing 70. At the other end rods 73 are attached to valgus pivot 68.

Ring assembly 74 has a variable ulna clamp 76 on the inside thereof, as best seen in FIG. 1. Padding and soft goods 80 are attached to screw clamps for comfort. Screw clamps 76 are adjustable to compensate for variations in the size of a patient's distal radius and ulna as well as centering the patient's limb along the pro/supination axis 82. The center of ring assembly 74 is concentric with pro/supination axis 82. The softgoods 80 of the pro/supination assembly 26 are secured to the ulna clamping mechanism 76. The softgoods 80 provide a comfortable patient interface and drive point for the distal radius and ulna. The softgoods 80 can accommodate a range of wrist flexion and deviation positions when secured to the pro/supination drive.

Figure 6:
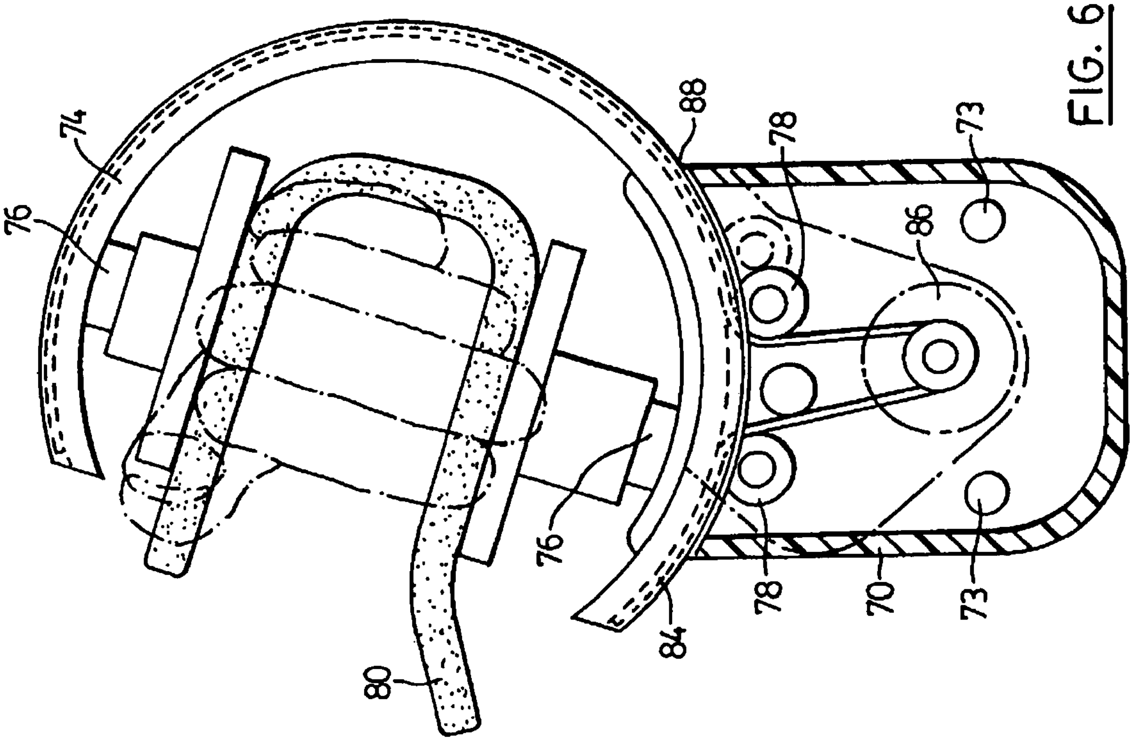
FIG. 6 is an enlarged front view of the combination pro-supination and flexion therapeutic mobilization device with a portion broken away showing the device in a different position from the position shown in FIG. 5.
Figure 5:
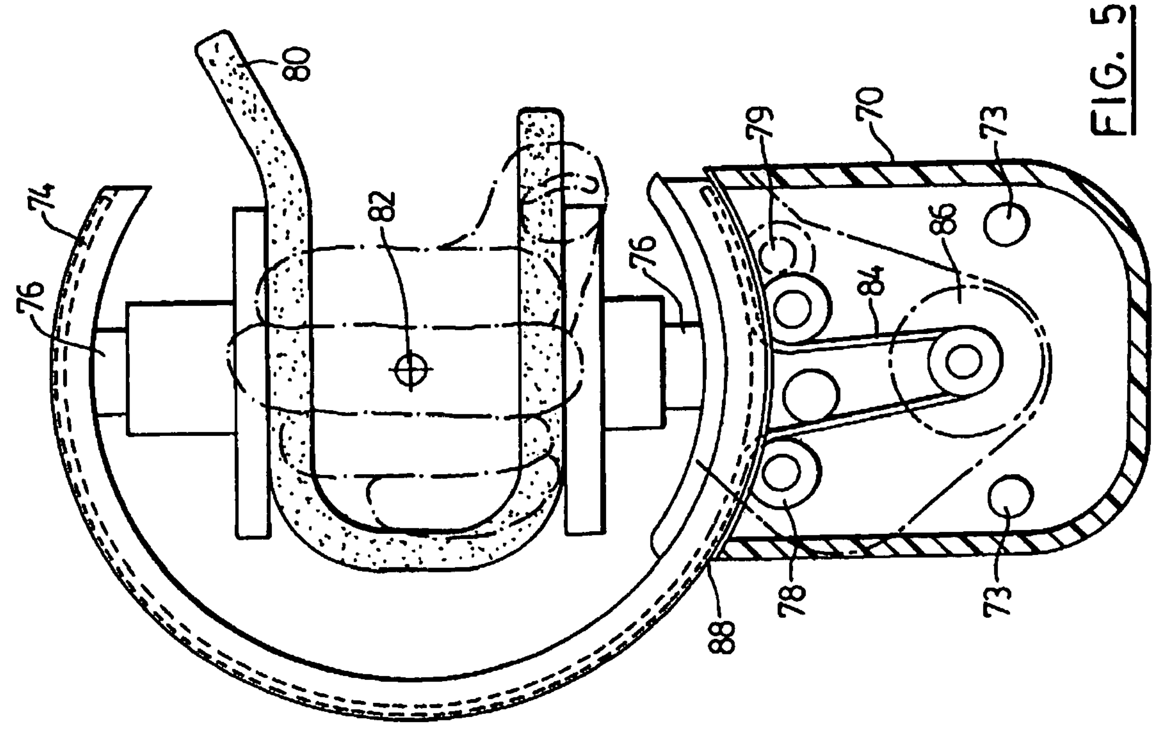
FIG. 5 is an enlarged front view of the combination pro-supination and flexion therapeutic mobilization device with a portion broken away.
Figure 7:
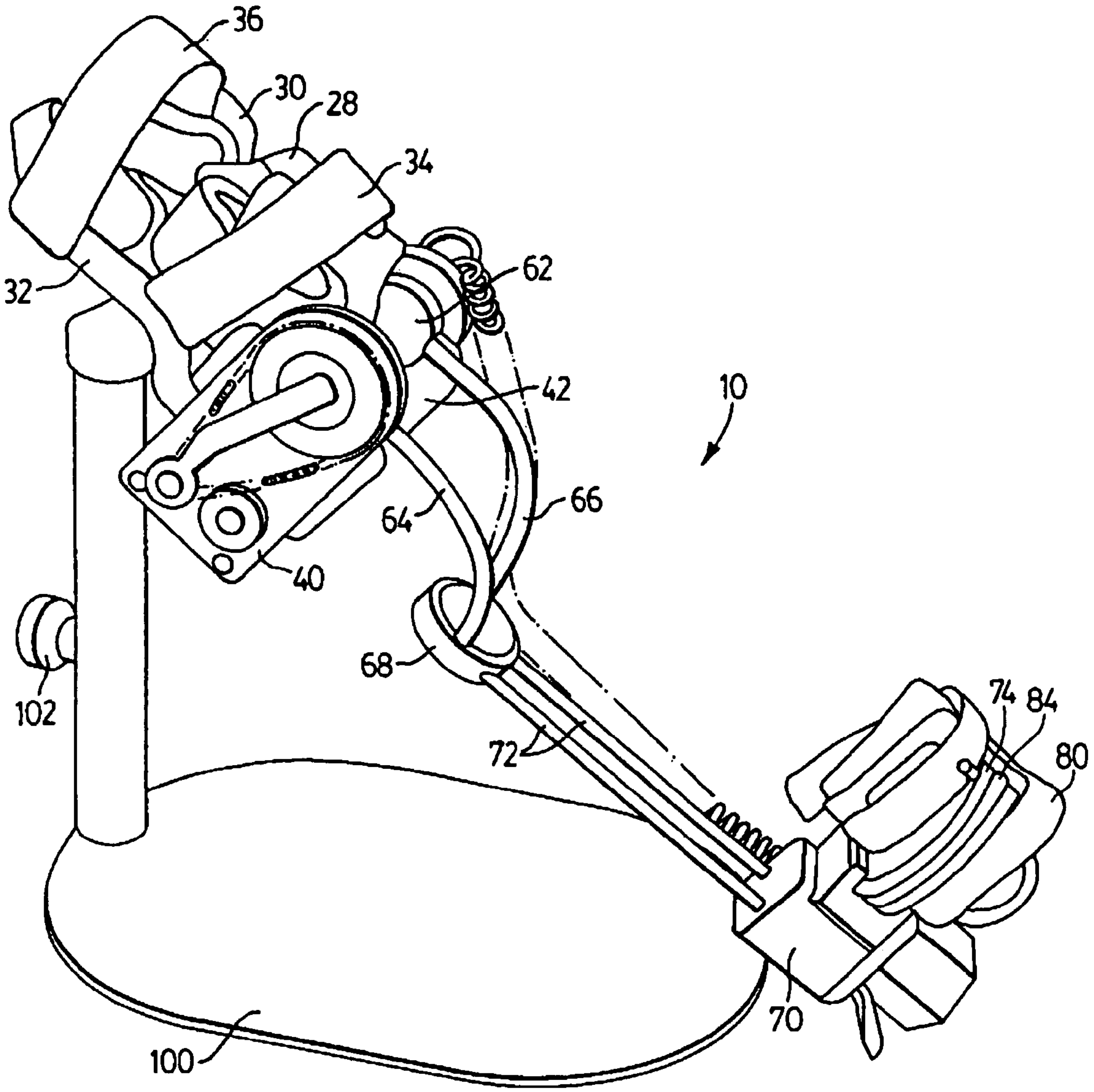
FIG. 7 is a perspective view of the combination pro-supination and flexion therapeutic mobilization device showing the device attached to a stand.
Figure 8:
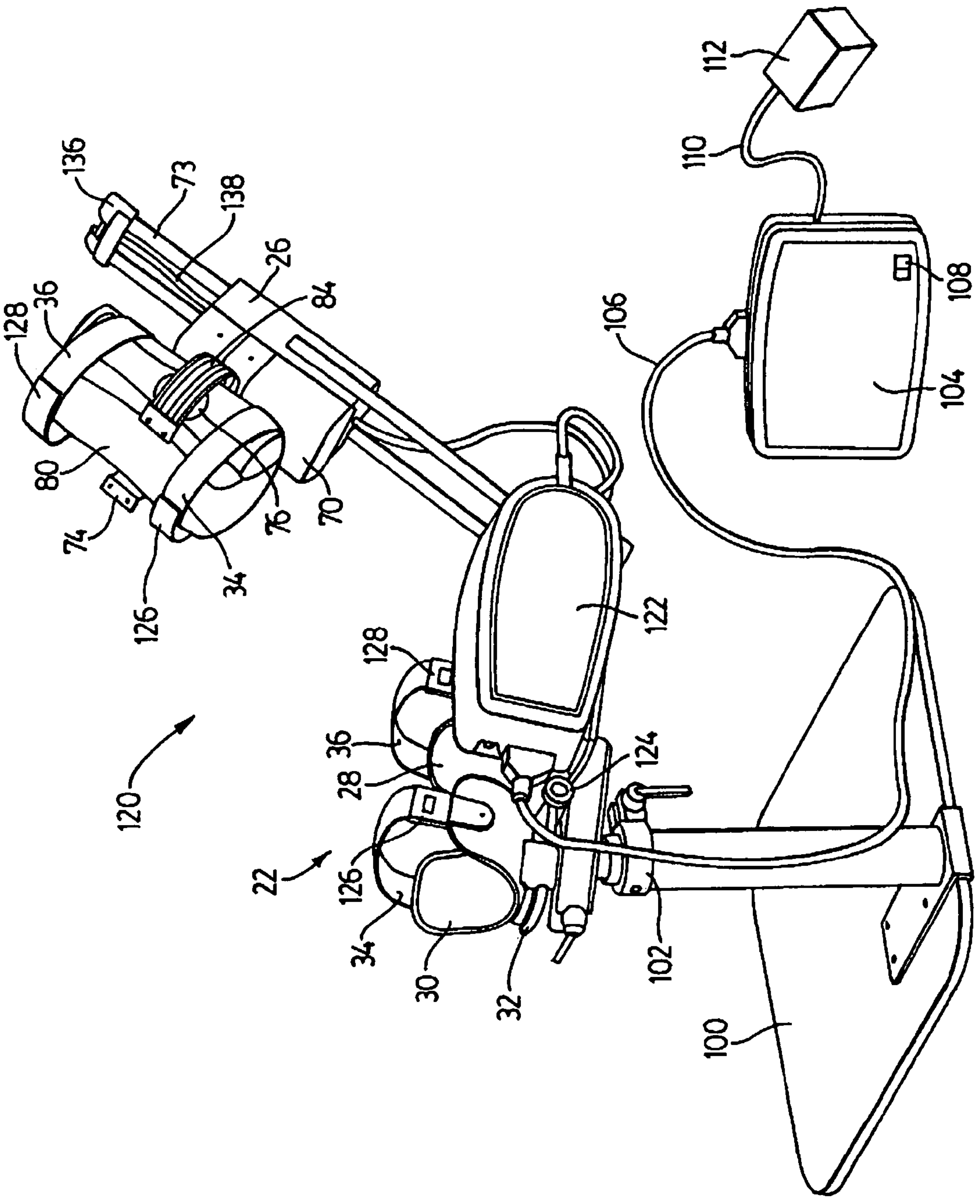
FIG. 8 is a perspective lateral view of an alternate embodiment of the combination pro/supination and flexion therapeutic mobilization device constructed in accordance with the present invention.

Ring assembly 74 is slidably mounted in pro/supination housing 70. An external belt 84 moves the ring in a rotational fashion relative to pro/supination housing 70. Referring to FIGS. 5 and 6, pro/supination housing 70 includes a pro/supination actuator 86 which drives the belt 84 which in turn drives the ring assembly 74. Idlers 78 help to keep belt 84 taut and in position. A ring channel 88 is formed in the pro/supination housing 70 so that the ring assembly rotates around its center which is concentric with the pro/supination axis 82. The ring assembly 74 is sized to allow the distal portion of the forearm of the patient to be positioned and secured in the center of the ring assembly 74. The pro/supination axis 82 is arranged such that it is concentric with the anatomic axis of the patient's forearm. The pro/supination housing 70 is slidably mounted in a radial fashion relative to the elbow axis 56. The ulna clamp device 76 secures the patient's distal radius and ulna too effectively transfer flexion and pro/supination from the humerus to the forearm. Preferably the ulna clamp device 76 is secured against the patient's distal radius and ulna wrist bone however it will be appreciated by those skilled in the art that ulna clamps could be secured to the patient anywhere along the ulna.

As shown in FIG. 2 valgus pivot 68 includes a top disc 90, a middle disc 92, a bottom disc 94 and a center pin 96 which holds them in pivotal arrangement. Top disc 90 is attached to first drive stay 64. Middle disc 92 is attached to second drive stay 66. Bottom disc 94 is attached to housing rods 73. Each of the discs can move independently of the others thus stays 64 and 66 and housing rods 73 can rotate relative to each other. Pivot 68 compensates for the variations in valgus carrying angle and the adjustable distance between the elbow actuators. Thus the valgus carrying angle is compensated for in a pivot 68 located between the elbow actuator's 40, 42 drive stays 64, 66 and the rods 73 that allow the pro/supination drive to slidably move.

Figure 13:
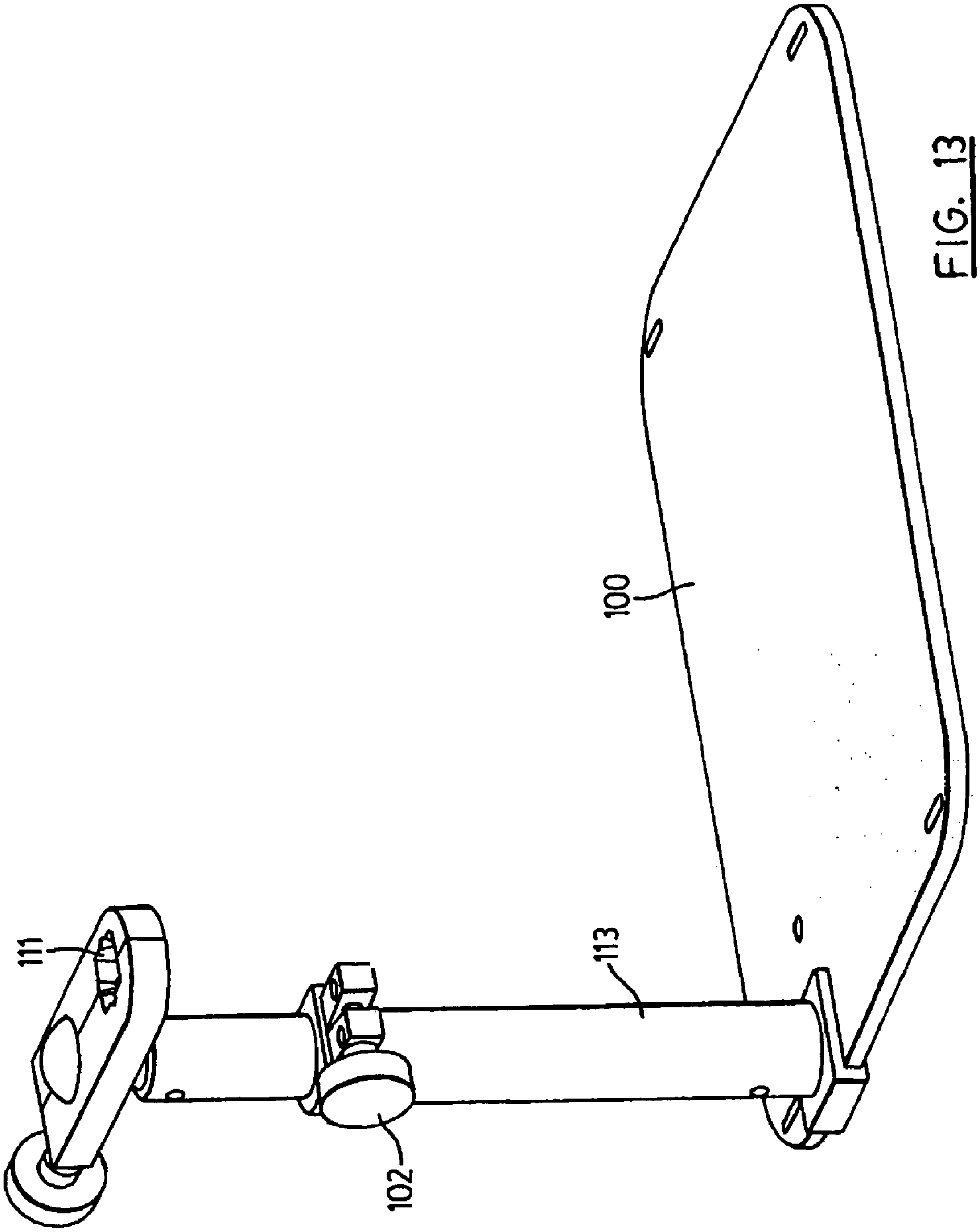
FIG. 13 is a perspective view of the mounting stand for use in association with the therapeutic mobilization device of the present invention.

A mounting feature on the orthosis allows the device to be secured to a bed, chair or ambulatory feature. As shown in FIGS. 7, 8, 9 and 13, devices 10 and 120 (described below) may be mounted on a stand 100. Referring to FIG. 13 a mounting receptacle 111 is attached to a mounting post 113. Mounting post 113 is telescopic and its height is adjusted by adjusting knob 102.

The anatomical features are to compensate and align the orthosis' actuators with the anatomic axis of the elbow and forearm. These features serve to minimize stress on the joint and surrounding soft tissue as the device moves through its range of motion.

Device 10 includes a patient controller 104. Device 10 is electrically connected to the patient controller 104 by cord set 106. Switch 108 on patient controller 104 turns the device 10 off and on. Patient controller 104 is connected to power supply 112 via cable 110. Patient controller 104 contains rechargeable batteries and can supply power to device 10 with or without being connected to a wall outlet.

With all of the therapeutic motion and splint devices it is important to align the device appropriately.

Referring to FIGS. 9 through 12 an alternate embodiment of an elbow and forearm therapeutic mobilization device or pro/supination flexion mobilization device is shown generally at 120. Only those elements different from those described above will be described herein in detail. Those elements which are the same will be referred to by the same number.

The mobilization device 120 includes an upper arm or humerus support 22, an elbow or flexion actuator assembly 122 and a wrist or pro/supination assembly 26.

The upper arm or humerus support 22 includes a lower or distal humerus cuff 28 and an upper or proximal humerus cuff 30. Proximal humerus cuff 30 is slidably mounted with respect to humerus support 22 via two parallel rods 32 and secured in position by lock knobs 124. A distal cuff strap 36 is attached to the distal humerus cuff 28 and a proximal cuff humerus strap 34 is attached to the proximal humerus cuff 30. Straps 34 and 36 use hook and loop type fastener in conjunction with buckles 126 and 128 to allow for easy attachment and adjustment. The distance between the distal humerus cuff 28 and the proximal humerus cuff 30 can be adjusted to ensure that mobilization device 120 is securely attached to the patient.

An L-shaped member 146 attaches humerus support 22 to elbow actuator assembly 122. The orientation of the humerus support 22 can be changed by depressing a button 148 that engages one of a pair of aperture 150 and then rotating humerus support 22 until it engages the other of aperture 150. A mounting post 152 is adapted to engage mounting receptacle 111. Mounting post 152 includes a quick release button 154 for disengaging device 120 from stand 100. Elbow actuator assembly 122 is mounted on L-shaped member 146 with a mount 156. Mount 156 includes electronic switches 158.

Figure 10:
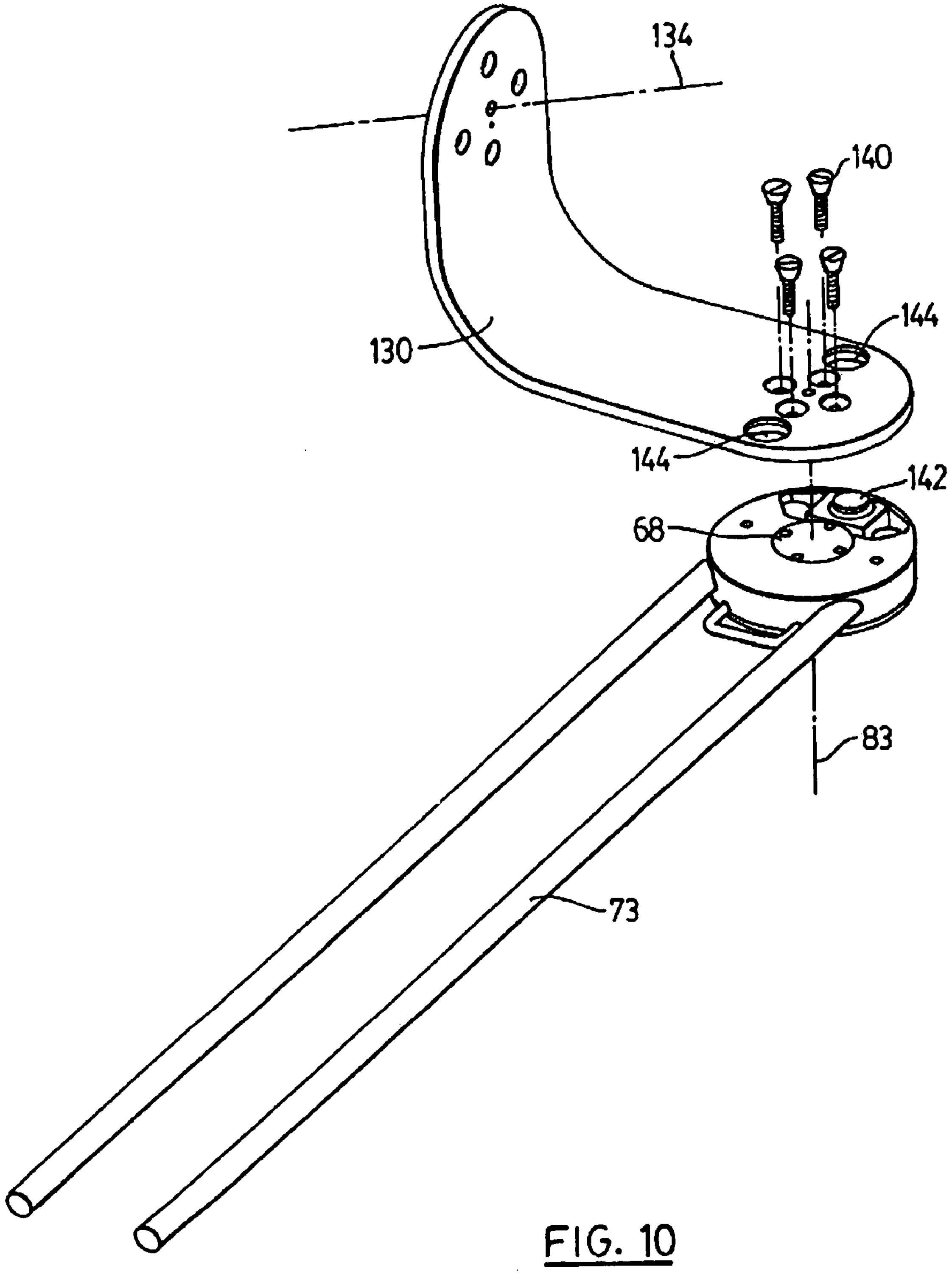
FIG. 10 is an enlarged perspective view of the valgus pivot of the combination pro/supination flexion therapeutic mobilization device shown in FIGS. 8 and 9.
Figure 11:
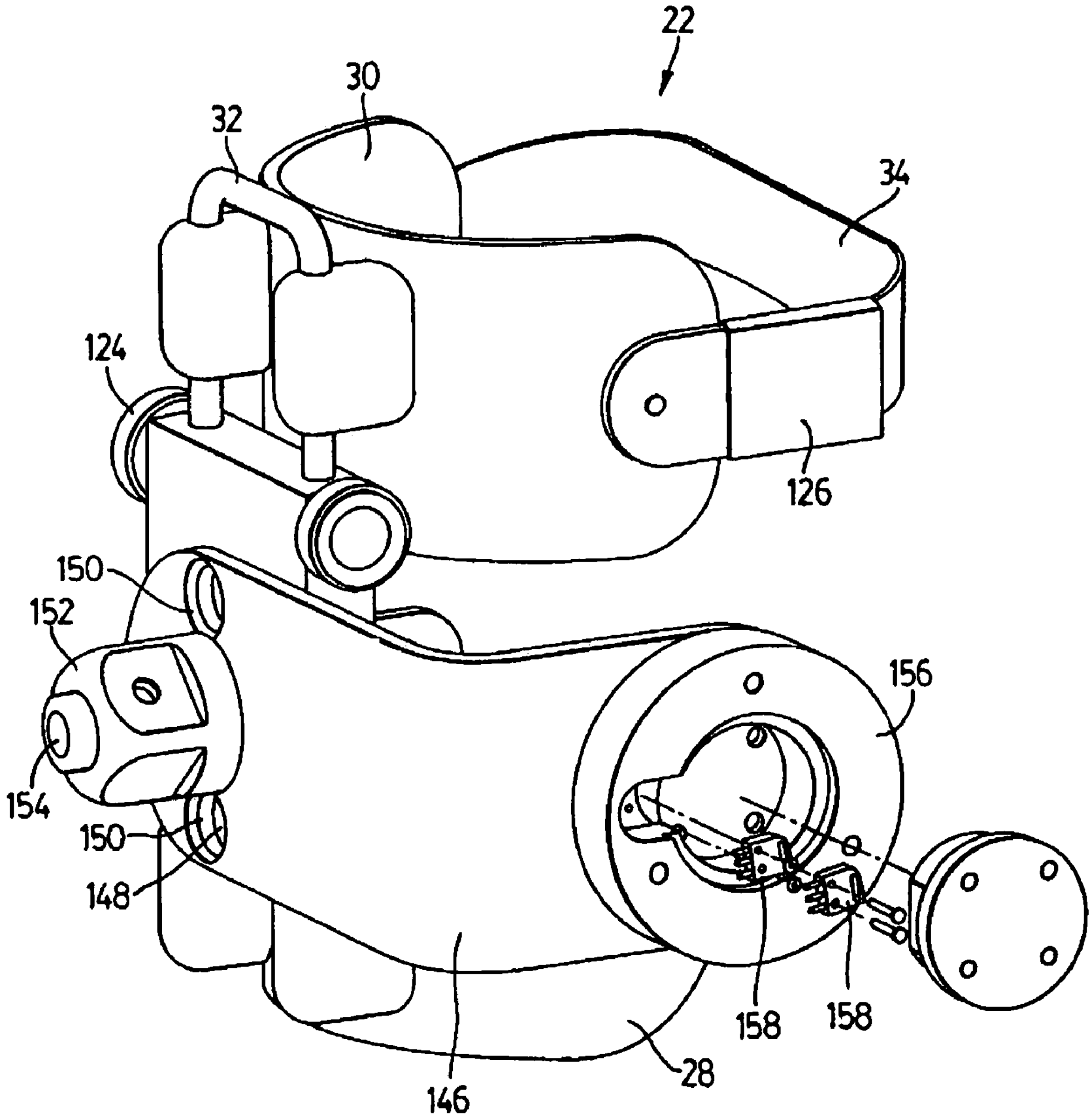
FIG. 11 is an enlarged perspective view of the humerus support and flexion actuator assembly of the therapeutic mobilization device shown in FIGS. 8–10.
Figure 12:
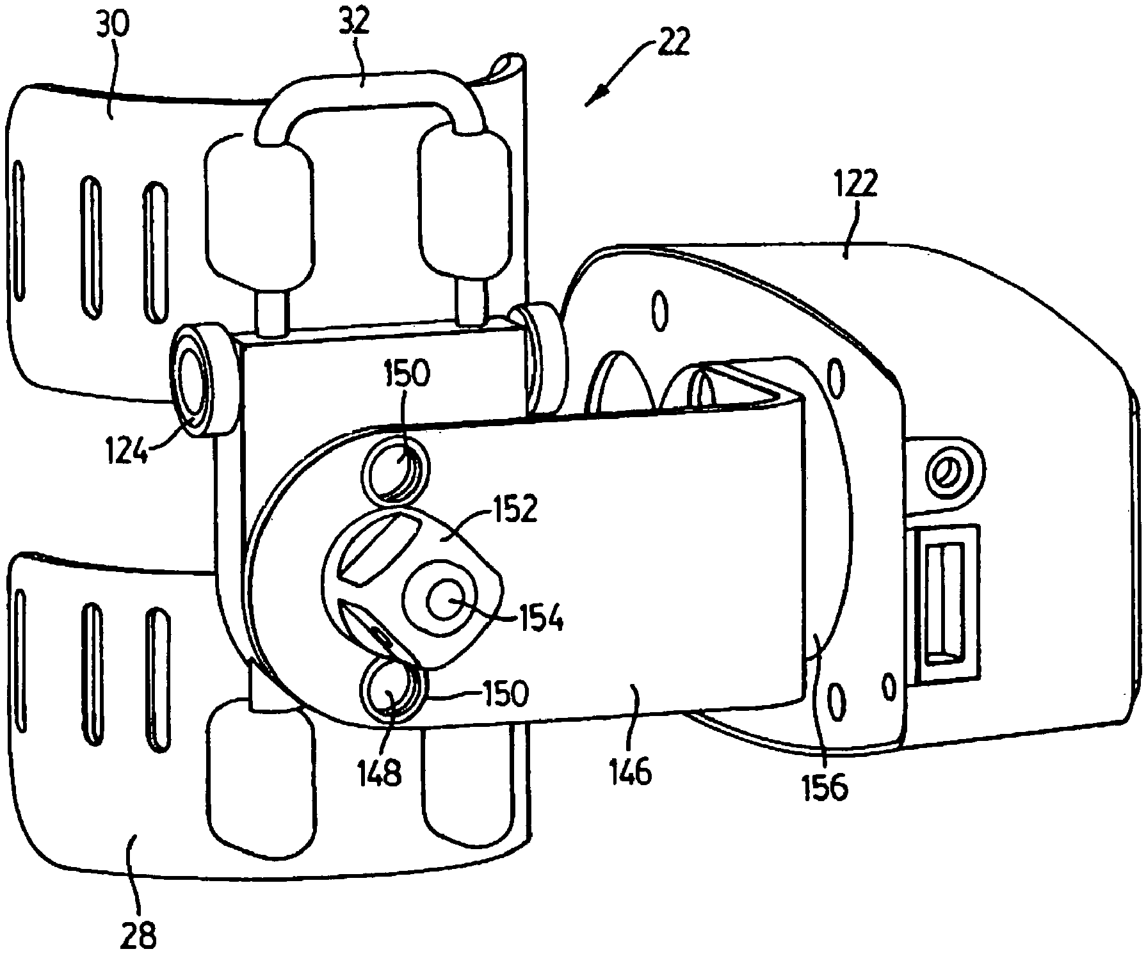
FIG. 12 is an enlarged perspective view of the humerus support of the therapeutic mobilization device shown in FIGS. 8–11.

The elbow actuator assembly 122 includes an orthosis stay 130 and is pivotally connected to actuator 122 at 132 and pivots around the elbow flexion rotational axis 134 as best seen in FIG. 10. Pivot point 132 of orthosis stay 130 is concentric with the elbow pivot axis 134. Orthosis stay 130 is pivotally connected at one end to flexion/elbow actuator assembly 122. The distal end of orthosis stay 130 is connected to valgus pivot 68 as best seen in FIG. 10. Pro/supination assembly 26 is attached to valgus pivot 68 via rods 73. Orthosis stay 130 is attached to valgus pivot 68 by a plurality of fasteners 140. A retractable button 142 engages one of the two opposing positioning aperture 144 in orthosis stay 130. The aperture 144 that is engaged determines the orientation of the rods 73 relative to the orthosis stay 130.

Pro/supination assembly 26 includes a pro/supination housing 70, a ring assembly 74, a variable distal forearm clamping device 76 and pair of parallel rods 73. Pro/supination actuator housing 70 is slidably mounted to parallel rods 73 and is limited in distal sliding range by end stop 136. An elastomeric tether 138 is attached between end stop 136 and pro/supination assembly 26. Elastomeric tether 138 compensates for the weight of the pro/supination assembly 26 and reduces the stress on the users elbow that would be exerted on the patient from the pro/supination assembly.

Figure 9:
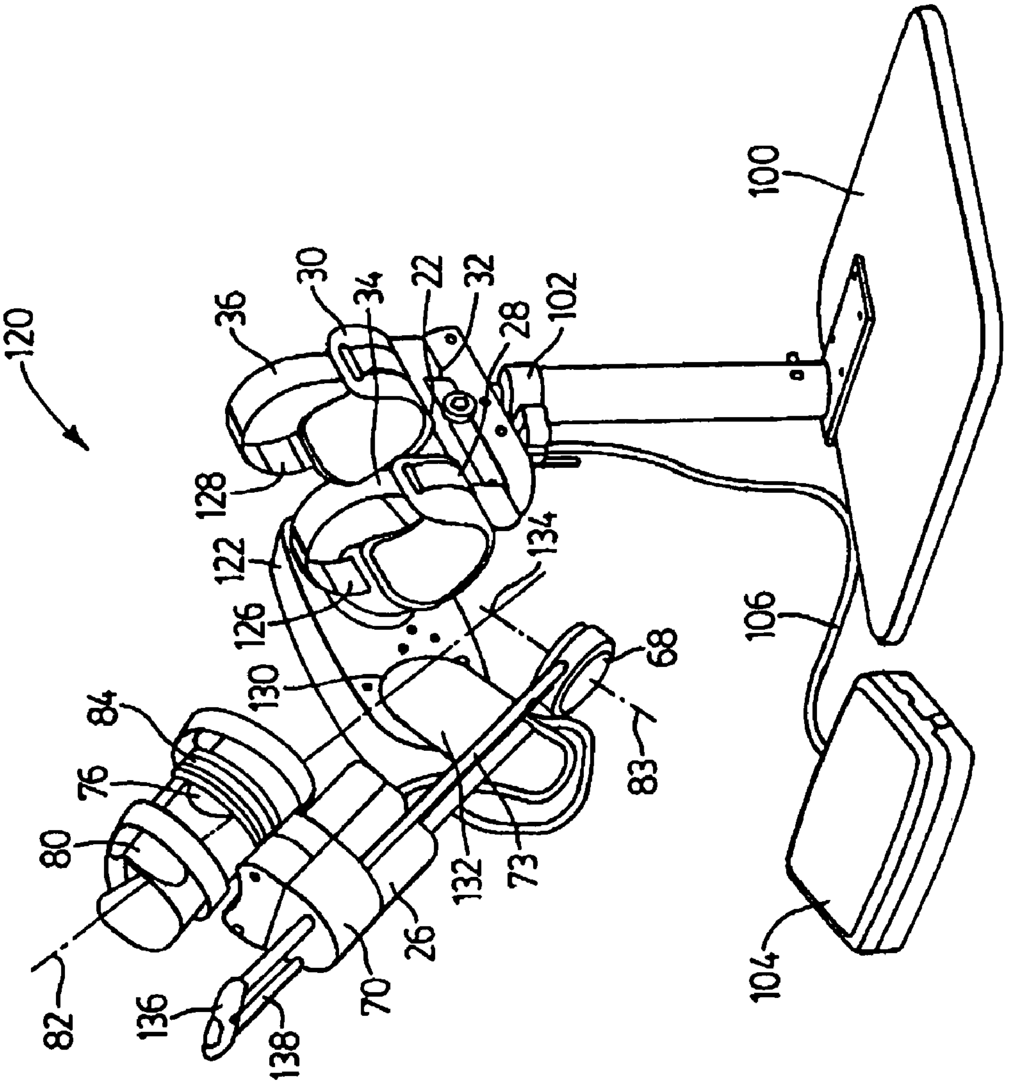
FIG. 9 is a perspective medial view of the combination pro/supination and flexion therapeutic mobilization device shown in FIG. 8.

Ring assembly 74 has a variable distal forearm clamp 76 on the inside thereof, as best seen in FIG. 9. Padding and soft goods 80 are pivotally attached to screw clamps for comfort. Padding and soft goods 80 are attached such that they can pivot around an axis that is orthogonal to pro/supination axis 82. Screw clamps 76 are adjustable to compensate for variations in the size of a patient's distal radius and ulna as well as centering the patient's limb along the pro/supination axis 82. The center of ring assembly 74 is concentric with pro/supination axis 82. The softgoods 80 provide a comfortable patient interface and drive point for the distal radius and ulna. The softgoods 80 can accommodate a range of wrist flexion and deviation positions when secured to the pro/supination assembly 26.

Ring assembly 74 is slidably mounted in pro/supination actuator housing 70. An external belt 84 moves the ring in a rotational fashion relative to pro/supination actuator housing 70. The pro/supination axis 82 is arranged such that it is concentric with the anatomic axis of the patient's forearm when positioned in the device 120. The pro/supination housing 70 is slidably mounted in a radial fashion relative to the valgus pivot axis 83, 134. The forearm clamp assembly 76 and softgoods 80 secure the patient's distal radius and ulna to effectively transfer flexion and pro/supination from the humerus to the forearm. Preferably the forearm clamp assembly 76 and softgoods 80 are secured against the patient's distal ulna and radius. However it will be appreciated by those skilled in the art that ulna clamps 76 could be secured to the patient anywhere along the ulna.

Mobilization device 120 may be mounted on a stand 100 and the height is adjustable with adjusting knob 102. Mobilization device 120 includes a patient controller 104. Device 120 is electrically connected to the patient controller 104 by cord set 106. Switch 108 on patient controller 104 turns the device 120 off and on. Patient controller 104 is connected to power supply 112 via cable 110. Patient controller 104 contains rechargeable batteries and can supply power to device 120 with or without being connected to a wall outlet.

Valgus pivot 68 compensates for the variations in carrying angle. The carrying angle is compensated for in a valgus pivot 68 located between the elbow actuator's 122, orthosis stay 130, and the pro/supination assembly slidably mounted on rods 73. The valgus pivot 68 compensates for misalignment of the patient in the device when it is first attached and during treatment. It minimizes the stresses that are caused by misalignment of the device. The sliding of the pro/supination assembly helps to compensate for the distraction and compression forces during use.

The mobilization device 120 is arranged such that only one adjustment is required to accommodate a range of patients with different sized arms and forearms. Only the proximal humerus cuff 30 is adjusted between patient sizes to accommodate differences in upper arm circumferences and differences in position of the arm's elbow anatomic axis relative to the posterior surface of the arm. This is accomplished by the pro/supination assembly 26 being slidably mounted along rods 73 and having a pivot at the ulna clamping device 76. The anatomical features are to compensate for and align the orthosis' actuators with the anatomic axis of the elbow and forearm and these features serve to minimise stress on the joint and surrounding soft tissue as the device moves through its range of motion.

Mobilization device 120 is designed to easily be adjusted. The device 120 is asymmetrical with the flexion actuator assembly 122 being positioned on the lateral side of the treated arm to minimise abduction while being treated and improve patient comfort. The device 120 can be converted to treat the left and right arm by unlocking and pivoting three components once it is removed from stand 100. To convert the device from left to right the user unlocks and pivots the humerus support 22, the flexion/elbow actuator assembly 122 and valgus pivot 68.

In use mobilization devices 10 and 120 are suitable for bed, chair and ambulatory use configurations. The devices 10 and 120 are symmetrical and ambidextrous. Each device 10, 120 offers a full range of variable elbow flexion. Each device 10, 120 also offer a full range of variable pronation and supination motion for the forearm. These motions are available in a synchronized motion, independently or in a serial motion. If pro/supination is programmed in a serial motion, preferably pro/supination will occur at 90 degrees of elbow flexion or as close thereto as possible. This is to limit stress on the joints. The device may be controlled by a hand held user interface allowing the operator to adjust the speed of travel (CPM mode only), range of motion, pause time at end of cycle and reverse on load. The device may have a means to electronically lock the patient settings while still allowing the patient to adjust the speed. The orthosis of the device is configured to provide anatomical elbow flexion and forearm pro/supination. The orthosis also compensates for the valgus carrying angle. The valgus carrying angle is the result of the lateral migration of the distal radius and ulna relative to the distal humerus as the forearm supinates. The orthosis also compensates for the anthropometric variances between patients. This is achieved by accommodating differences in arm circumference, length and anatomical axis relative to the exterior surfaces of the arm. The device integrates a novel arrangement of strain gauges to monitor the amount of force in flexion and torque in pro/supination the device is delivering to the involved limb. The anatomical features are to compensate for and align the orthosis' actuators with the anatomic axis of the elbow and forearm. These features serve to minimize stress on the joint and surrounding soft tissue as the device is moved or is positioned through its range of motion.

Figure 14:
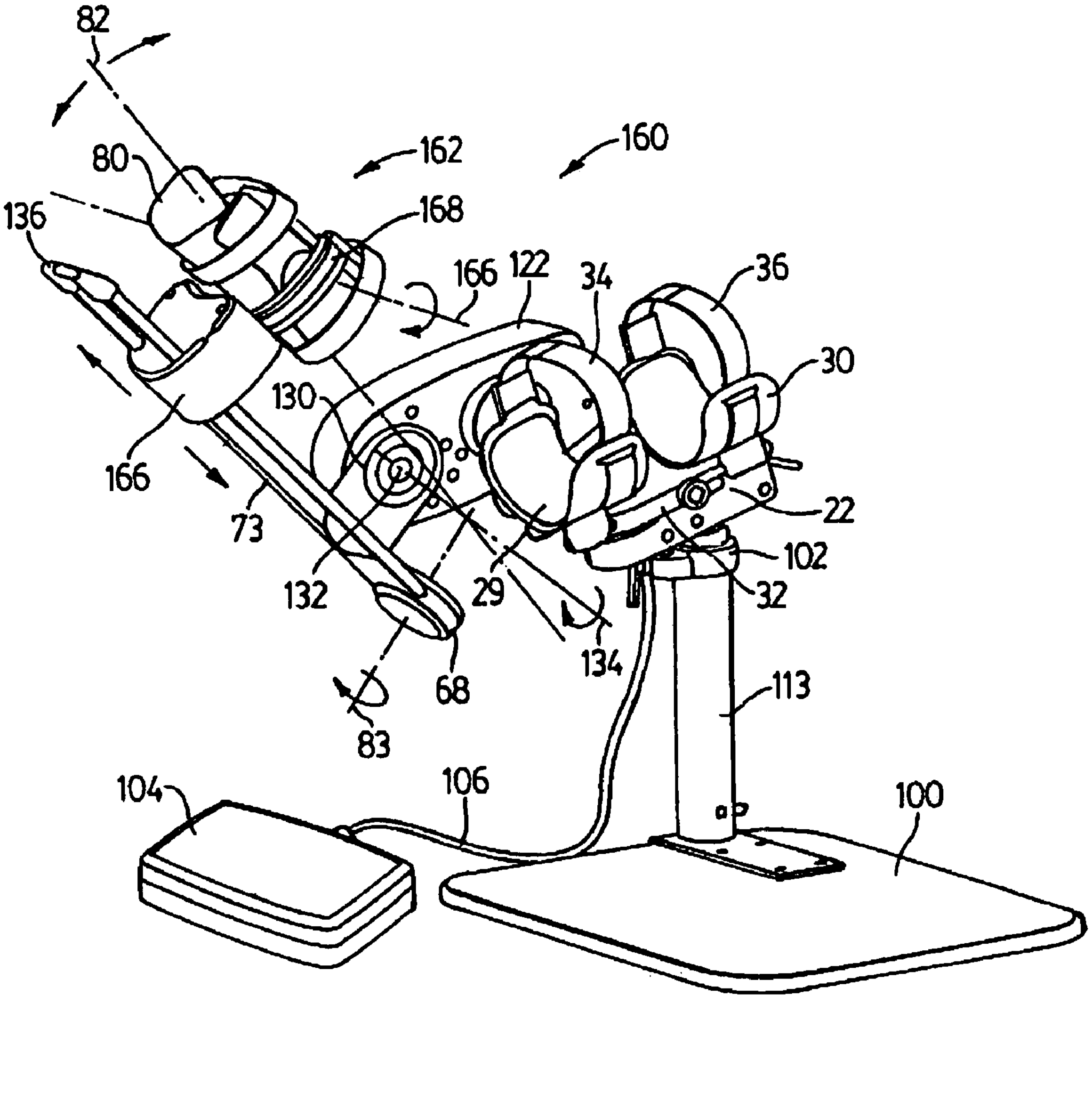
FIG. 14 is a perspective view of a flexion therapeutic mobilization device constructed in accordance with the present invention.

Referring to FIG. 14 another alternative embodiment of the present invention is shown generally at 160. Device 160 is solely a flexion device that is similar to device 120 but it does not include a pro/supination assembly. Rather than a pro/supination assembly, device 160 includes an arm support 162. Arm support is slideably mounted on rods 73. Arm support has a support ring 168 attached to a housing 166. Soft goods 80 are pivotally attached to support ring 168 and can rotate around axis 82. The remainder of device 160 is similar to that described above with regard to device 120.

Figure 15:
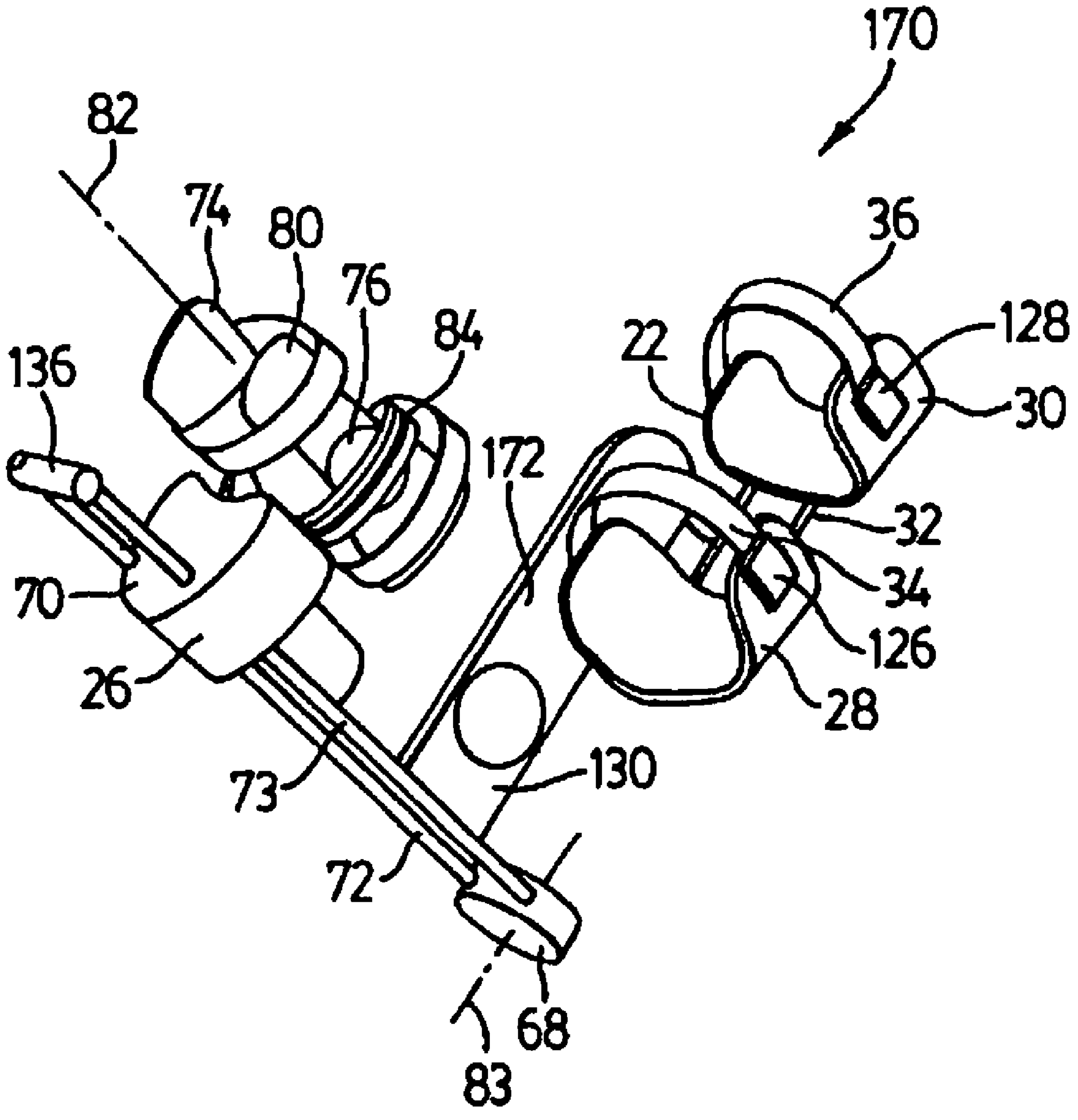
FIG. 15 is a perspective view of a pro/supination mobilization device constructed in accordance with the present invention.

Similarly it will be appreciated by those skilled in the art that elements of the present invention could be used for a pro/supination only device wherein the flexion actuator was not used or not included in the device at all. As shown in FIG. 15, a pro/supination mobilization device 170 may also be constructed in accordance with the present invention. Device 170 includes an upper arm support 22 and a pro/supination assembly 26. As discussed above the pro/supination assembly 26 includes a pro/supination housing 70 slidably mounted on parallel rods 73, a ring assembly 74 and a ulna clamping device 76. Housing shaft 72 includes a pair of parallel rods 73. Rods 73 have and end stop 136 at one end thereof and at the other end thereof are attached to valgus pivot 68 having a valgus pivot axis 83.

Ring assembly 74 has a variable ulna clamp 76 on the inside thereof. Padding and soft goods 80 are attached to screw clamps for comfort. The center of ring assembly 74 is concentric with pro/supination axis 82. Ring assembly 74 is slidably mounted in pro/supination housing 70. An external belt 84 moves the ring in a rotational fashion relative to pro/supination housing 70.

The upper arm support 22 includes a lower or distal humerus cuff 28 and an upper or proximal humerus cuff 30. Cuff 30 is slidably mounted along cuff support 32. A lower cuff strap 34 is attached to the lower humerus cuff 28 and an upper cuff humerus strap 36 is attached to the proximal humerus cuff 30. An L-shaped orthosis stay 130 is pivotally connected at one end thereof to an elongate connector 172 and at the other end thereof it is connected to the vulgas pivot 68. The elongate connector 172 is also attached to the upper arm support 22.

It will be appreciated that the above description related to the invention by way of example only. Many variations on the invention will be obvious to those skilled in the art and such obvious variations are within the scope of the invention as described herein whether or not expressly described.

What is claimed as the invention is:

1. A therapeutic mobilization device for use with a patient comprising:

a flexion assembly having an arm attachment means and an elbow actuator having an elbow axes of rotation;

a pronation/supination assembly operably attached to the flexion assembly, the pronation/supination assembly having a distal forearm attachment means and a pronation/supination actuator operably connected thereto; and a valgus carrying angle compensation device operably attached between the flexion assembly and the pronation/supination assembly whereby the valgus carrying compensation device compensates for misalignment of the patient in the device, thereby reducing stresses during use.

2. A therapeutic mobilization device as claimed in claim 1 wherein the valgus carrying angle compensation device includes a pivot operably attached between the distal forearm attachment means and the arm attachment means.

3. A therapeutic mobilization device as claimed in claim 2 wherein the pivot is a flexible member.

4. A therapeutic mobilization device as claimed in claim 2 wherein the pivot is an adjustable linkage.

5. A therapeutic mobilization device as claimed in claim 1 wherein the elbow actuator includes a first and second spaced apart elbow actuator and the flexion assembly further includes at least one orthosis rod and an adjustable assembly moveably attached between the first and second spaced apart elbow actuators whereby selectively adjusting adjustable assembly causes the first and second actuators to move towards and away from each other along a path defined by the orthosis rod.

6. A therapeutic mobilization device as claimed in claim 5 wherein the orthosis rod is shaped such that as the first and second elbow actuators move away from each other, each moves forwardly relative to the arm attachment means.

7. A therapeutic mobilization device as claimed in claim 6 further including a second orthosis rod slideably attached between the first and second elbow actuators.

8. A therapeutic mobilization device as claimed in claim 1 wherein the elbow actuator is attached to the arm attachment means and an orthosis stay is rotatably attached to the elbow actuator and to the valgus carrying angle compensation device whereby rotation of the orthosis stay moves the user's elbow through flexion.

9. A therapeutic mobilization device as claimed in claim 8 wherein the valgus carrying angle compensation means is a pivot.

10. A therapeutic mobilization device as claimed in claim 9 wherein the pronation/supination assembly includes a housing shaft and the distal forearm attachment means is slideably mounted on the housing shaft whereby during flexion distal forearm attachment means is free to move along the housing shaft.

11. A therapeutic mobilization device as claimed in claim 10 wherein the housing shaft defines a pronation/supination axis and wherein the distal forearm attachment means includes a distal forearm clamp pivotally attached to a pronation/supination housing whereby the distal forearm clamp pivots orthogonally to the pronation/supination axis.

12. A therapeutic mobilization device as claimed in claim 11 wherein the elbow actuator is pivotally attached to the arm attachment and has a first elbow position and a second elbow position and the pivot has a first pivot position and second pivot position and whereby the first elbow position and first pivot position define a right hand orientation and the second elbow position and the second pivot position define a left hand orientation.

13. A therapeutic mobilization device as claimed in claim 1 wherein the pronation/supination assembly is slideably attached to a housing shaft which is attached to the valgus carrying angle compensation device.

14. A therapeutic mobilization device as claimed in claim 2 wherein the pronation/supination assembly is slideably attached to a housing shaft.

15. A therapeutic mobilization device as claimed in claim 14 wherein the pronation/supination assembly further includes a pronation/supination housing, an attachment ring rotatably attached to the housing and distal forearm attachment assembly attached thereto, a belt attached to the attachment ring and to the pronation/supination actuator whereby actuation of the pronation/supination actuator causes the belt to move the attachment ring in pronation and supination.

16. A therapeutic mobilization device as claimed in claim 15 wherein the distal forearm attachment assembly includes an adjustable clamping mechanism having at least one adjustable clamp whereby selectively adjusting the adjustable clamping mechanism a patient's limb can be anatomically aligned and secured in the device.

17. A therapeutic mobilization device as claimed in claim 16 wherein the housing shaft defines a pronation/supination axis and wherein the adjustable clamping mechanism is pivotally attached to attachment ring whereby the adjustable clamping mechanism pivots orthogonally to the pronation/supination axis.

18. A therapeutic mobilization device for use with a patient comprising:

an arm attachment means;

a distal forearm attachment means;

a valgus carrying angle compensation device connected between the arm attachment means and the distal forearm attachment means whereby the valgus carrying compensation device compensates for misalignment of the patient in the device, thereby reducing distraction and compression forces during use; and an elbow actuator operably connected to the arm attachment means and the distal forearm attachment means whereby movement of the actuator causes the user to move through elbow flexion.

19. A therapeutic mobilization device as claimed in claim 18 wherein the valgus carrying angle compensation device is a pivot.

20. A therapeutic mobilization device as claimed in claim 19 wherein a housing shaft is attached to the pivot and the distal forearm attachment means is slidably attached to the pivot.

21. A therapeutic mobilization device as claimed in claim 20 wherein the distal forearm attachment means includes an attachment ring and an adjustable clamping mechanism pivotally attached to the ring whereby the housing shaft defines a pronation/supination axis and the adjustable clamping mechanism pivots orthogonally to the pronation/supination axis.

* * * * *